United States Patent [19]

Olesen et al.

[11] Patent Number: 5,475,015
[45] Date of Patent: Dec. 12, 1995

[54] BENZIMIDAZOLE DERIVATIVES, THEIR PREPARATION AND PHARMACEUTICAL USE

[75] Inventors: Søren-Peter Olesen, Klampenborg; Leif H. Jensen, Copenhagen; Peter Moldt, Humlebæk, all of Denmark

[73] Assignee: NeuroSearch A/S, Glostrup, Denmark

[21] Appl. No.: 206,506

[22] Filed: Mar. 4, 1994

[30] Foreign Application Priority Data

Mar. 15, 1993 [DK] Denmark ................. 0288/93

[51] Int. Cl.$^6$ ............ A61K 31/415; C07D 235/04; C07D 487/00
[52] U.S. Cl. ................. 514/387; 548/306.4; 548/307.1
[58] Field of Search ............ 548/306.4, 307.1; 514/387

[56] References Cited

U.S. PATENT DOCUMENTS 5,200,422  4/1993  Olesen et al. ............ 514/387

*Primary Examiner*—Johann Richter
*Assistant Examiner*—Laura L. Stockton
*Attorney, Agent, or Firm*—Gordon W. Hueschen

[57] ABSTRACT

A compound having the formula

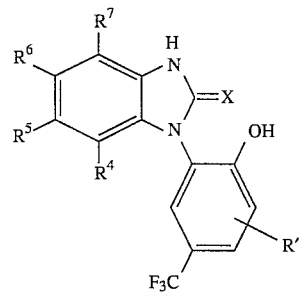

wherein
X is O, S
$R^4$, $R^5$, $R^6$ and $R^7$ independently of each other are hydrogen, halogen, or $CF_3$;
R' is hydrogen or $NO_2$; and
further a method of treating a disorder or disease of a living animal body, including a human, which is responsive to opening of potassium channels, which comprises administering to a living animal body, including a human, in need thereof an effective amount of a compound as above.

8 Claims, No Drawings

BENZIMIDAZOLE DERIVATIVES, THEIR PREPARATION AND PHARMACEUTICAL USE

The present invention relates to novel benzimidazole derivatives, a method of preparing the same, a method of treatment with the novel benzimidazole derivatives, and to pharmaceutical compositions comprising the same.

OBJECT OF THE INVENTION

It is an object of the present invention to provide novel benzimidazole compounds which are useful in the treatment of disorders or diseases of a living animal body, including a human, and especially in the treatment of disorders and diseases which can be treated by opening cell membrane potassium channels of such living animal bodies.

Another object of the present invention is to provide a method of treating a disorder or disease of a living animal body, including a human, which is responsive to opening of potassium channels and which comprises administering to such a living animal body, including a human, in need thereof, a compound of the invention.

A third object of the present invention is to provide novel pharmaceutical compositions for the treatment of disorders or diseases of a living animal body, including a human, which are responsive to the opening of potassium channels.

Other objects will be apparent to the skilled person hereinafter.

BACKGROUND OF THE INVENTION

Bianchi et al. in Eur. J. Med. Chem.—Chimica Therapeutica 16(4), 321–326 (1981) discloses benzimidazolino2-on derivatives having anti-ulcer and anti-secretory activity. Clark et al. in J. Med. Chem. 21(9), 965–978 (1978) discloses imidazo[4,5 -b]pyridin-2-on derivatives having analgesic activity.

European patent application Publication No 477819 discloses related compounds which are openers of BK channels.

It is generally well known that opening of potassium (K+) channels leads to a hyperpolarization and relaxation of cells. The presently known K+ channel openers (e.g. cromakalim and pinacidil) exert their effect primarily via the K+ channel subtype $K_{ATP}$. They have a high affinity for vascular smooth muscle cells and are thus mostly vasodilators. Recent studies indicate, however, that K+ channel openers hyperpolarizing neuronal cells also have anticonvulsive and antiischemic effects in the central nervous system (the CNS) (European Journal of Pharmacology 167, 181–183 (1989), Neuroscience Letters 115, 195–200 (1990), Neuroscience 37(1), 55–60 (1990), The Journal of Pharmacology and Experimental Therapeutics 251 (1), 98–104 (1989)). Furthermore recent studies demonstrate that potassium channel openers acting on airways smooth muscle (tracheal smooth muscle) cells will have anti-asthmatic effects (Williams et al., The Lancet 336, 334–336 (1990).

There exist other K+ channel subtypes than $K_{ATP}$, and one such subtype is the BK channel, also called the maxi-K channel or large-conductance, $Ca^{2+}$ dependent K+ channel. The BK channel is present in many cells including most central and peripheral nerve cells, striated muscle cells, smooth muscle cells of the airways, the vasculature, the gastrointestinal tract and bladder, in endo- and exocrine glands including pancreatic β-cells and in kidney tubules (R. Latorre et al., Annu. Rev. Physiol. 51, 385 (1989).

A scorpion toxin peptide, charybdotoxin, which blocks the BK channel fairly specifically, has been used to demonstrate that the BK channel plays an important role as a relaxing negative feed-back when the cells in these tissues become highly active or spastic (J. E. Brayden and M. T. Nelson, Science 256, 532 (992; T. R. Jones et al., J. Pharmacol. Exp. Ther. 255, 697 (1990); R. Robiteille and M. P. Charlton, J. Neurosci. 12, 297 (1992); G. Suarez-Kurtz et al., J. Pharmacol. Exp. Ther. 259, (1991)).

SUMMARY OF THE INVENTION

The invention then, inter alia, comprises the following, alone or in combination:

A compound having the formula

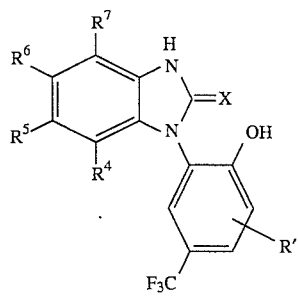

wherein

X is O, S $R^4$, $R^5$, $R^6$ and $R^7$ independently of each other are hydrogen, halogen, or $CF_3$;

R' is hydrogen or $NO_2$;

and a compound as above which is 5-trifluoromethyl-2, 3-dihydro-1-(5 -trifluoromethyl-2-hydroxyphenyl)-1H-2-oxo-benzimidazole, and a compound as above which is 5-trifluoromethyl-2, 3-dihydro-1-(5 -trifluoromethyl-2-hydroxyphenyl)-1H-2-thio-benzimidazole, and a compound as above which is 5-trifluoromethyl-2, 3-dihydro-1-(3-nitro-5 -trifluoromethyl-2-hydroxyphenyl)-1H-2-oxo-benzimidazole, further a method of treating a disorder or disease of a living animal body, including a human, which is responsive to opening of potassium channels and which comprises administering to such a living animal body, including a human, in need thereof an effective amount of a compound as first above, and a method as above wherein arterial hypertension, coronary artery spasms, asthma, irritable bowel syndrome, spastic bladder, ischemia, psychosis, or convulsions are treated, and a method as above wherein the compound is administered in the form of a pharmaceutical composition thereof, in which it is present together with a pharmaceutically acceptable carrier or diluent, and further a pharmaceutical composition comprising a therapeutically-effective amount of a compound as first above together with a pharmaceutically-acceptable carrier, and further a method of preparing a compound as first above which comprises the step of reacting a compound having the formula

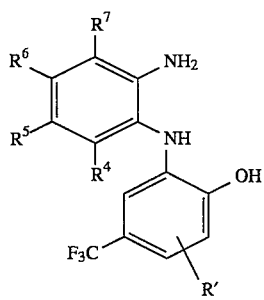

wherein R', R⁴, R⁵, R⁶, and R⁷ have the meanings set forth above with phosgene, an urea derivative, or thiocarbonyl diimidazol.

Biological Activity

The compounds of the present invention are potent openers of the BK channel, and the ability of the compounds of the present invention to open the BK channel can be demonstrated in several ways.

All experiments were performed with patch-clamp technique (Hamill et al., Pflügers Arch. 391, 85–100 (1981)). The ion composition of the internal solution was (in mM) 140 KCl, 1 CaCl$_2$, 1 MgCl$_2$, 2 EGTA, 10 HEPES and the external solution contained 140 NaCl, 4 KCl, 2 CaCl$_2$, 1 MgCl$_2$ and 10 HEPES.

Whole Cell Recordings

The membrane potential of calf aortic smooth muscle cells was determined in whole-cell recordings using current clamp mode (HEKA EPC-9 patch-clamp amplifier). Due to the high-resistance seal and the large size of these cells the recorded membrane potential stayed stable for periods of 30–60 min, although at somewhat depolarized values (−58− −22 mV). Administration of for example 1-(5-trifluoromethyl-2-hydroxyphenyl)-5-trifluoromethyl-1,3-dihydro-2H-benzimidazol-2-one (10 μM) to the bath hyperpolarized the cells after a delay of 1–3 min. The average hyperpolarization was −20 mV (SD=−9 mV, n=7), and the effect was largest in the cells being most depolarized prior to administration of the compound.

The equilibrium potential for K+, Cl−, and Na+ in these experiments were −90 mV, 0 mV, and +90 mV, respectively (cf. ion composition above). Thus, since potassium is the only ion having a reversal potential more negative than the resting membrane potential the observed hyperpolarization induced by the test compound must be explained through an increased potassium conductance.

The whole cell currents through the smooth muscle cell membrane was also determined. The compounds at concentrations of 3–30 μM specifically activated BK currents, blockable by charybdotoxin, by increasing the outward current by up to 10 times and shifting the activation curve by more than −50 mV towards negative membrane potentials.

A selective activation of BK currents was also found in cultured cortical neurons, cerebellar granule cells and pancreatic β-cells. No effect was found on Na+ currents or voltage-dependent K+ currents (A type, delayed rectifier type) also present in these cells.

Single Channel Experiments

In inside-out patches of cerebellar granule cell membrane single BK channels were activated by for example 5-trifluoromethyl1-(5-trifluoromethyl-2 -hydroxyphenyl)-1,3-dihydro-2H-benzimidazole-2-one (3 μM). The compound increased the open probability of the BK channel with several hundred percent. No effect was found on the delayed rectifier K+ channel or on the Cl− channels also present in the patches.

Likewise in cultured bovine aortic smooth muscle cells in which the BK is the predominant K+ channel for example 1,3-dihydro-1-(5-trifluoromethyl-2 -hydroxyphenyl)-5-trifluoromethyl-2H-benzimidazole-2-one (3 μM) significantly activated the BK channel.

Guinea-Pig Ileum Experiment

The compound, 5-trifluoromethyl-1-(5-trifluoromethyl-2-hydroxyphenyl)-1,3 -dihydro-2H-benzimidazole-2-one, has been studied for its ability to relax acetylcholine-contracted guinea-pig ileum. The smooth muscle cells of the ileum express many BK channels and the model predicts relaxing effects on the gastrointestinal or urogenital tracts. The above mentioned compound relaxes the ileum in a dose-dependent way (3–30 μM). The effect of 30 μM compound is reversed by the BK channel blocker TEA+ (1–3 mM), confirming that the relaxing effect is mediated via BK channels.

Method: Ileum from guinea-pigs are isolated and mounted in an isometric contraction chamber. It is bathed in a physiological Krebs solution at 98° F. The ileum is precontracted with increasing concentrations of acetylcholine (0.015–5.0 μM). The contractions are reversed by including the compound in the bathing solution.

Trachea Experiment

The compound, 5-trifluoromethyl-1-(5-trifluoromethyl-2-hydroxyphenyl)-1,3 -dihydro-2H-benzimidazole-2-one, has been studied in a trachea model in which relaxation predicts anti-asthmatic potential. The above mentioned compound relaxes trachea in a dose-dependent way (10–100 μM) and 10 μM compound also potentiates the relaxing effect of lemakalim by 10 x.

Method: Guinea pig trachea is isolated with intact vagus nerve. Tubes are inserted into both ends and ligated tightly so the pressure in the fluid-filled lumen can be monitored. Electrical stimulation of the vagus nerve leads to a contraction and a pressure increase. The difference in electrically-stimulated pressure increase in the absence and presence of compound is measured.

Cocaine Experiment

The compound, 5-trifluoromethyl-1-(5-trifluoromethyl-2-hydroxyphenyl)-1,3 -dihydro-2H-benzimidazole-2-one, has been studied in the cocaine motility test. Cocaine induces hypermotility due to an inhibition of dopamine reuptake. The test is recognized as a test predicting anti-psychotic activity. The above mentioned compound potently (1–10 mg/kg) antagonizes cocaine induced hypermotility according to the test procedure described below. 5-Trifluoromethyl 1-(5-trifluoromethyl-2-hydroxyphenyl-1,3-dihydro-2H-benzimidazole-2-one (30 mg/kg) produces by itself a weak hyperactivity.

Method: Two female NMRI mice (20–25 g) are placed in each test box (normal transparent plexiglas cage, w, l, h=21×39×19 cm ) in the test room for at least 16 hours with food and water ad libitum before the test in order for the animals to habituate to the situation. The test compound is administered i.p. 15 min before saline or 25 mg/kg cocaine i.p. to 32 mice (16 boxes) per dose. Food and water are withdrawn, and the motility is measured as the number of interrupted infrared photo-beams (8 per box placed 5 cm apart and 3 cm over the bottom of the cage) in the next 120 min. The results obtained demonstrate that the compounds of the invention are potential anti-psychotics acting by a novel discovered mechanism.

Pharmaceutical Compositions

While it is possible that, for use in therapy, a compound of the invention may be administered as the raw chemical, then it is preferable to present the active ingredient as a pharmaceutical formulation.

The invention thus further provides a pharmaceutical formulation comprising a compound of the invention or a pharmaceutically acceptable salt or derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting vax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting vax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water propylene glycol solutions. For example, parenteral injection liquid preparations can be formulated in solutions in aqueous polyethylene glycol solution.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising the active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasel cavity by conventional means, for example with a dropper, pipette or spray. The formulations may be provided in single or multidose form. In the latter case of a dropper or pipette this may be achieved by the patient administering an appropriate, predetermined volume of the solution of suspension. In the case of a spray this may be achieved for example by means of a metering atomizing spray pump.

Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of disorders of a living animal body, including a human, due to their potent potassium channel activating properties. These properties make the compounds of this invention extremely useful in the treatment of potassium channel dependent convulsions, potassium channel dependent asthma, potassium channel dependent arterial hypertension, potassium channel dependent coronary artery spasms, potassium channel dependent irritable bowl, potassium channel dependent spastic bladder, potassium channel dependent ischemia, and other disorders sensitive to potassium channel activating activity. The compounds of this invention may accordingly be administered to a subject, including a human, in need of treatment, alleviation, or elimination of an indication associated with the potassium channels. This includes especially convulsions and every form of epilepsy, asthma, hypertension, spastic bladder, irritable bowl, coronary artery spasms, aterial hypertension, psychosis and ischemia.

Suitable dosage range are 0.1–1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

EXAMPLE 1

2-Methoxy-5-trifluoromethyl-aniline.

2-Methoxy-5-trifluoromethyl-nitrobenzene (283 mmol, 62,67 g) suspended in ethanol (500 ml) is hydrogenated over palladium on carbon 5% (1.7 g) and the reaction mixture is filtered through celite. The filtrate is concentrated in vacuo yielding the title compound as light grey crystals M.p. 61° C.

EXAMPLE 2

N-(2-methoxy-5-trifluoromethylphenyl)-4-trifluoromethyl-2-nitroaniline.

To an ice cooled solution of 2-Methoxy-5-trifluoromethylaniline (311 mmol, 59.4 g) in 500 ml dry dimethylformamide is added sodiumhydride (438 mmol, 17.5 g 60%) followed by slow addition of 2-chloro-5-trifluoromethylnitrobenzene (311 mmol, 47.4 ml) and the mixture is stirred for 60 hours. More sodiumhydride (10 g 60%) is added and after stirring for additional two hours is another portion of 2-chloro-5-trifluoromethyl-nitrobenzene (5 ml) and sodiumhydride (2 g 60%) added. Upon completion is the reaction mixture poured into water and a black precipitate is formed. The crude product is filtered of and is washed with 1M HCl and petroleum ether yielding the title compound as grey crystals, M.p. 86°–88° C.

EXAMPLE 3

N-(2-amino-4-trifluoromethylphenyl)-2-methoxy-5-trifluoromethylaniline, hydrochloride.

N-(2-Methoxy-5-trifluoromethylphenyl)-4-trifluoromethyl-2-nitroaniline (302 mmol, 115 g) dissolved in ethanol (900 ml) is hydrogenated over palladium on carbon 5% (1.5 g) and the reaction mixture is filtered through celite into concentrated hydrochloric acid (30 ml) in ethanol (100 ml). The filtrate is concentrated in vacuo yielding the title compound as grey crystals M.p. 186° C.

EXAMPLE 4

N-(2-Ethoxycarbonylamino-4-trifluoromethylphenyl)-2-methoxy-5-trifluoromethylaniline.

To an ice cooled suspension of N-(2-amino-4-trifluoromethylphenyl)-2 -methoxy-5-trifluoromethylaniline, hydrochloride (300 mmol, 116 g) in 600 ml absolute methylene chloride is added triethylamine (900 mmol, 125 ml) followed by ethylchloroformiate (600 mmol, 63 ml). The reaction mixture is stirred at room temperature for 18 hours followed by concentration in vacuo. The remanence is triturated with water and the crude product is washed with small amounts of diethylether. Filtration yields the title compound as white crystals, which is used without further purification.

EXAMPLE 5

1-(2-Methoxy-5-trifluoromethylphenyl)-5-trifluoromethyl-1,3-dihydro-2 H-benzimidazol-2-one.

To an ice cooled suspension of N-(2-ethoxycarbonylamino-4 -trifluoromethylphenyl)-2-methoxy-5-trifluoromethylaniline (140 mmol, 59 g) in 200 ml absolute ethanol is added sodium (174 mmol, 4 g) and the mixture is stirred at 70° C. for four hours. When the reaction is completed the reaction mixture is poured into water which is acidified and the title compound is collected by filtration as white crystals, M.p. 226° C.

1-(2-Methoxy-5-trifluoromethylphenyl)-5-trifluoromethyl-1,3-dihydro-2H-benzim idazol-2-thione.

To an ice cooled suspension of N-(2-amino-4-trifluoromethylphenyl)-2-methoxy- 5-trifluoromethylaniline, hydrochloride (3 mmol, 1.2 g) in dry methylenechloride (20 ml) is added triethylamine (9 mmol, 0.73 ml) and thiophosgene (3 mmol, 0.23 ml). The reaction mixture is stirred at room temperature overnight and poured into water. The mixture is extracted with methylenechloride and the organic phases are dried and concentrated in vacuo. The crude product is subjected to column chromatography using petroleum ether+ethylacetate (4+1) as eluent. The fractions containing the product are concentrated in vacuo yielding a yellow oil which solidifies upon treatment with petroleum ether, yielding the title compound as off white crystals, which were used without further purification.

EXAMPLE 6

1-(2-Hydroxy-5-trifluoromethylphenyl)-5-trifluoromethyl-1,3-dihydro-2 H-benzimidazol-2-one.

A suspension of 1-(2-Methoxy-5-trifluoromethylphenyl)-5-trifluoromethyl-1,3 -dihydro-2H-benzimidazol-2-one (70 mmol, 26.3 g) in absolute methylenechloride is added borontribromide (84 mmol, 7.94 ml). After stirring at room temperature for four hours the reaction mixture is poured into water and the title compound is collected by filtration as white crystals, M.p. 228°–231° C.

The following compound is prepared in a similar manner.

1-(2-Hydroxy-5-trifluoromethylphenyl)-5-trifluoromethyl-1,3-dihydro-2 H-benzimidazol-2-thione, M.p. decompose at 160° C.

EXAMPLE 7

1-(2-Hydroxy-3-nitro-5-trifluoromethylphenyl)-5-trifluoromethyl-1,3-dihydro-2 H-benzimidazol-2-one.

To an ice cooled solution of 1-(2-Hydroxy-5-trifluoromethylphenyl)-5 -trifluoromethyl-1,3-dihydro-2H-benzimidazol-2-one (1.38 mmol, 0.50 g) in concentrated sulphuric acid (6 ml) is added an ice cooled solution of potassium nitrate (1.38 mmol, 0.14 g) in concentrated sulphuric acid (8 ml). The reaction mixture is allowed to reach room temperature and is poured into ice. The crude product is collected by filtration and subjected to column chromatography using methylenechloride+methanol (9+1 ) as eluent. The fractions containing the product are concentrated in vacuo yielding the title compound as slightly yellow crystals, M.p.>360° C.

We claim:

1. A compound having the formula

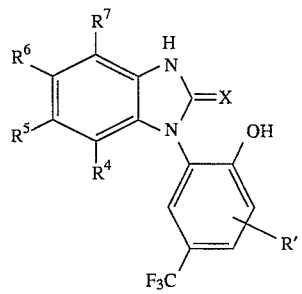

wherein

X is O, S $R^4$, $R^5$, $R^6$ and $R^7$ independently of each other are hydrogen, halogen, or $CF_3$;

R' is hydrogen or $NO_2$.

2. A compound of claim 1 which is 5-trifluoromethyl-2,3-dihydro-1-(5 -trifluoromethyl-2-hydroxyphenyl)-1H-2-oxo-benzimidazole.

3. A compound of claim 1 which is 5-trifluoromethyl-2,3-dihydro-1 -(5-trifluoromethyl-2-hydroxyphenyl)-1H-2-thio-benzimidazole.

4. A compound of claim 1 which is 5-trifluoromethyl-2,3-dihydro-1-(3-nitro-5 -trifluorom ethyl-2-hydroxyphenyl)-1H-2-oxo-benzim idazole.

5. A method of treating a disorder or disease of a living animal body, which is responsive to opening of potassium channels, and which comprises administering to such a living animal body, in need thereof an effective amount of a compound of claim 1.

6. A method of claim 5 wherein arterial hypertension, coronary artery spasms, asthma, ischemia, irritable bowl syndrome, spastic bladder, psychosis or convulsions are treated.

7. A method of claim 5 wherein the compound is administered in the form of a pharmaceutical composition thereof, in which it is present together with a pharmaceutically acceptable carrier or diluent.

8. A pharmaceutical composition comprising a therapeutically-effective amount of a compound of claim 1 together with a pharmaceutically-acceptable carrier.

\* \* \* \* \*

UNITED STATES PATENT AND TRADEMARK OFFICE
CERTIFICATE OF CORRECTION

PATENT NO. : 5,475,015
DATED : Dec. 12, 1995
INVENTOR(S) : Soren-Peter Olesen, Leif H. Jensen, Peter Moldt It is certified that error appears in the above-indentified patent and that said Letters Patent is hereby corrected as shown below:

Column 1, line 34: "benzimidazolino2-" should read -- benzimidazolino-2- --.

Column 3, line 38: "Administration of ...." should start a new paragraph.

Column 4, line 1: "luoromethyl1-" should read -- luoromethyl-1- --.

Column 4, line 58: Add a -- - -- (dash) at the end of the line.

Column 8, line 48: Add a -- - -- (dash) at the end of the line.

Column 8, line 49: Delete the " - "(dash) from the beginning of the line.

Column 8, line 52: "of" should read -- off --.

UNITED STATES PATENT AND TRADEMARK OFFICE
CERTIFICATE OF CORRECTION

PATENT NO. : 5,475,015
DATED : Dec. 12, 1995
INVENTOR(S) : Soren-Peter Olesen, Leif H. Jensen, Peter Moldt It is certified that error appears in the above-indentified patent and that said Letters Patent is hereby corrected as shown below:

Column 9, line 30: "benzim idazol-" should read -- benzimidazol- --.

Column 10, line 43: "trifluorom ethyl-" should read -- trifluoromethyl --.

Column 10, line 44: "benzim idazole." should read -- benzimidazole. --.

Signed and Sealed this

Second Day of April, 1996

BRUCE LEHMAN

Attest:

Attesting Officer

Commissioner of Patents and Trademarks